United States Patent
Nagai

(10) Patent No.: US 9,797,826 B2
(45) Date of Patent: Oct. 24, 2017

(54) OPTICAL ANALYZER

(71) Applicant: SHIMADZU CORPORATION, Kyoto-shi, Kyoto (JP)

(72) Inventor: Yusuke Nagai, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 8 days.

(21) Appl. No.: 14/922,250

(22) Filed: Oct. 26, 2015

(65) Prior Publication Data
US 2016/0187250 A1 Jun. 30, 2016

(30) Foreign Application Priority Data

Dec. 25, 2014 (JP) .................................. 2014-261503

(51) Int. Cl.
*G01N 21/00* (2006.01)
*G01N 22/00* (2006.01)
*G01N 21/25* (2006.01)

(52) U.S. Cl.
CPC ... *G01N 21/255* (2013.01); *G01N 2201/0624* (2013.01)

(58) Field of Classification Search
CPC ..................... G01N 21/255; G01N 2201/0624
USPC ................................................. 356/335–344
See application file for complete search history.

(56) References Cited

U.S. PATENT DOCUMENTS

| | | | | |
|---|---|---|---|---|
| 3,820,901 A * | 6/1974 | Kreuzer | ............... | G01N 21/314 250/345 |
| 4,269,509 A * | 5/1981 | Berry | ............... | G01J 3/44 356/301 |
| 4,594,511 A * | 6/1986 | Cooper | ............... | G01J 3/4338 250/338.1 |
| 4,937,448 A * | 6/1990 | Mantz | ............... | G01N 21/39 250/343 |
| 5,246,868 A * | 9/1993 | Busch | ............... | G01N 21/71 250/339.13 |
| 5,317,156 A * | 5/1994 | Cooper | ............... | G01N 21/39 250/339.13 |
| 5,572,031 A * | 11/1996 | Cooper | ............... | G01D 3/0365 250/343 |
| 5,821,537 A * | 10/1998 | Ishihara | ............... | G01J 3/433 250/339.13 |

(Continued)

FOREIGN PATENT DOCUMENTS

WO 2010/117026 A1 10/2010

*Primary Examiner* — Tri Ton
*Assistant Examiner* — Jarreas C Underwood
(74) *Attorney, Agent, or Firm* — Westerman, Hattori, Daniels & Adrian, LLP

(57) ABSTRACT

An optical filter 4 is placed in an optical path between a light source unit 1 using a deep ultraviolet LED as a light source and a sample cell 2. The optical filter 4 is a shortpass filter that allows passage of light of a main peak located within a deep ultraviolet region while blocking light of an unwanted peak located within a visible region. The temporal change in the amount of light of the unwanted peak is considerably greater than that of the main peak. The optical filter 4 blocks the former light whose amount considerably changes with time. As a result, the influence of the noise and drift originating from the LED on the detection signal obtained in a detector 3 is dramatically reduced, so that the analytical accuracy is improved.

3 Claims, 3 Drawing Sheets

(56) References Cited

U.S. PATENT DOCUMENTS

| | | | |
|---|---|---|---|
| 6,344,648 B1 * | 2/2002 | Boucher | G01N 21/39 |
| | | | 250/339.13 |
| 6,728,026 B2 * | 4/2004 | Lee | H01S 3/06758 |
| | | | 359/337.11 |
| 9,322,772 B2 * | 4/2016 | Ehring | G01N 30/74 |
| 9,664,564 B2 * | 5/2017 | Yoshida | G01J 3/30 |

* cited by examiner

OPTICAL ANALYZER

TECHNICAL FIELD

The present invention relates to an optical analyzer for casting light into or onto a target sample and for detecting transmitted light, fluorescent light, scattered light, diffracted light or other forms of light.

BACKGROUND ART

In a measurement of an absorbance of a liquid sample or gas sample, an optical analyzer is normally used, such as an ultraviolet-visible spectrophotometer or photodiode array detector. For example, an ultraviolet-visible spectrophotometer commonly uses a deuterium discharge tube as the light source for the ultraviolet region and a halogen lamp, as the light source for the visible region. In recent years, an ultraviolet-visible spectrophotometer using a xenon flash lamp (which has a longer life than the halogen lamp or deuterium discharge tube) has also been developed. In any case, optical analyzers using those light sources are normally configured so that monochromatic light is extracted by a monochromator using a diffraction grating or similar device and cast into or onto a sample, or so that light obtained from a sample is introduced into a light-dispersing device and dispersed into wavelengths components, which are then partially or entirely introduced into and detected by a detector.

In recent years, with the advancement and rapid spread of the light-emitting diode (LED) technology, LEDs have also been increasingly used as light sources in optical analyzers. Since LEDs have a comparatively narrow peak in their emission spectra, they are less suitable for applications which require the scan of a wide range of wavelengths. However, LEDs are suited to optical analyzers which casts a specific wavelength of light into or onto a sample, as in the case of an absorptiometer or fluorometer. LEDs are not only far more inexpensive than the previously mentioned light sources, but also have a long life and operate with high reliability. On the other hand, in general, the amount of light emitted from an LED considerably changes with the ambient temperature. In optical analyzers, such a change in the amount of light makes the measured result less accurate. Therefore, attempts have been made to reduce such an influence of the temperature dependency of the amount of light by controlling the temperature of the LED or controlling the drive current to the LED according to the temperature change so as to maintain the amount of light at a fixed level.

Nevertheless, those methods are not sufficient for performing a measurement with high accuracy. Accordingly, in an analyzer described in Patent Literature 1, in addition to the LED temperature control, a configuration is adopted in light of the fact that the degree of the temperature-dependent change in the amount of LED light is more noticeable at shorter wavelengths than at longer wavelengths. According to the configuration, an optical filter is placed in an optical path of the light emitted from the LED, for blocking light within a wavelength region shorter than the peak wavelength in the emission spectrum of the LED, i.e. within a region where the amount of light is particularly temperature dependent.

By the previously described methods, the problem of the measurement accuracy due to the temperature dependency of the amount of light emitted from an LED can be solved to a certain extent. However, even if such a factor is removed, an optical analyzer using an LED as a light source is inferior to optical analyzers using conventional light sources in that the detection signal contains a greater amount of noise and drift. Therefore, to further improve the measurement accuracy, it is essential to reduce the noise and drift originating from the light source.

As stated earlier, the peak width of an LED emission spectrum is normally narrow. This has led to the expectation that it may be possible to directly use LED light as measurement light without changing it to monochromatic light using an expensive light-dispersing device. However, for example, if light emitted from an LED is directly used as measurement light for absorbance analysis, the linearity of absorption will be low, in particular, within a high-absorbance region.

CITATION LIST

Patent Literature

Patent Literature 1: WO 2010-117026 A

SUMMARY OF INVENTION

Technical Problem

The present invention has been developed to solve the previously described problem. One of its objectives is to provide an optical analyzer which uses an LED or similar light-emitting semiconductor device as a light source and yet can perform an analysis with high accuracy by reducing the noise and drift originating from the light-emitting semiconductor device. Another objective of the present invention is to improve the linearity of the absorption of light in an optical analyzer which uses an LED or similar light-emitting semiconductor device as a light source.

Solution to Problem

In the emission spectrum of an LED, the intended peak is often accompanied by an unintended peak originating from an impurity contained in the crystal which appears within a shorter or longer wavelength region than the intended peak wavelength. For example, a deep ultraviolet LED which has a peak within a deep ultraviolet region of 200 to 350 nm often has another peak within a visible region of 400 to 600 nm. For an optical analyzer which uses a peak within the deep ultraviolet region as illumination light, the light having a peak within the visible region is useless for analysis. Conventionally, such unwanted light has not been regarded as a problem since its intensity is extremely low compared to the light within the wavelength region used for the analysis. However, experiments and other research activities by the present inventor have revealed that, although the amount of such unwanted light is certainly low, the temporal change in the amount of light is non-negligibly large, and the change in the amount of unwanted light constitutes a significant factor of noise and drift. Such a problem, to a greater or lesser extent, can also be found in other light-emitting semiconductor devices, such as a super luminescence diode (SLD), as well as in LEDs.

The first aspect of the present invention has been developed based on this finding to solve the previously described problem. That is to say, the first aspect of the present invention provides an optical analyzer for analyzing a target sample by casting light from a light source into or onto the sample and introducing light obtained from the sample in response to the cast light into a detector, the optical analyzer characterized in that a light-emitting semiconductor device is used as the light source and an optical filter is provided in an optical path from the light source to the detector, the optical filter blocking light within a range of wavelengths longer than the wavelength of a peak having the highest intensity in an emission spectrum of the light source, within a range of wavelengths shorter than the wavelength of the highest-intensity peak or within a range of wavelengths longer and shorter than the wavelength of the highest-intensity peak, and each of the ranges of wavelengths including a peak at which the temporal change in the amount of light is larger than that at the highest-intensity peak.

Examples of the light-emitting semiconductor device include light emitting diodes (LED), super luminescence diodes (SLD) and laser diodes (LD).

As noted earlier, a deep ultraviolet LED having the highest-intensity peak within the deep ultraviolet region often has another peak within the visible region, and the temporal change in the amount of light at this peak is larger than at the highest-intensity peak. Therefore, in the optical analyzer according to the first aspect of the present invention, the optical filter may preferably have such a characteristic as to block light at a peak appearing within a range of wavelengths longer than the wavelength of the highest-intensity peak in the emission spectrum of the light source.

In the optical analyzer according to the first aspect of the present invention, if the optical filter is placed in an optical path between the light source and the sample, the sample will be illuminated with light having an emission spectrum free of the peak at which the amount of light considerably changes with time. Accordingly, the light which has transmitted through or scattered by the illuminated sample does not contain the component of light corresponding to the aforementioned peak at which the amount of light considerably changes with time. Therefore, even if the detector is tuned to receive a wide range of wavelengths of light including the wavelength region of that component of light, the influence of the temporal change in the signal level originating from the light source will barely appear in the detection signal. As a result, the noise and drift in the detection signal are reduced.

The same effect can also be obtained by placing the optical filter in an optical path between the sample and the detector instead of the optical path between the light source and the sample.

A study by the present inventor has demonstrated that, within the wavelength region corresponding to the highest-intensity peak, the temporal change in the amount of light at a wavelength in the base portion of the peak waveform remote from the peak top is greater than at the wavelengths near the peak top. Accordingly, to further reduce the noise and drift, it is preferable to block not only the light at the unwanted peak different from the highest-intensity peak but also the light in the base portion of the highest-intensity peak.

That is to say, in the optical analyzer according to the first aspect of the present invention, the optical filter may have such a characteristic as to allow passage of light within a predetermined wavelength width centering on the wavelength of the highest-intensity peak in the emission spectrum of the light source and being narrower than the full width at half maximum of the highest-intensity peak and to block light within wavelength regions outside the aforementioned wavelength width.

Although LEDs and other light-emitting semiconductor devices have a narrow peak in their emission spectra, the full width at half maximum of the peak is normally larger than that of monochromatic light produced by a monochromator using a diffraction grating or similar device. Furthermore, as compared to the monochromatic light whose intensity falls in a comparatively steep way at both ends of the wavelength width of the monochromatic light since the light produced by the monochromator is extracted through a slit, the emission peak produced by a light-emitting semiconductor device has its base portions spread over a comparatively wide range. Therefore, using light emitted from a light-emitting semiconductor device without passing through a monochromator gives rise to a comparatively high amount of undesired light (i.e. stray light) other than the light of the target wavelength. In particular, the stray light is likely to affect the analysis when the absorbance is high and the light intensity is low. Such an effect of the stray light cannot be easily removed by correction or other data processing techniques. Reducing the influence of any stray light is favorable for improving the linearity of absorption. For that purpose, it is preferable to remove the largest possible amount of light in the base portions of the emission peak of the light-emitting semiconductor device.

Accordingly, the second aspect of the present invention provides an optical analyzer for analyzing a target sample by casting light from a light source into or onto the sample and introducing light obtained from the sample in response to the cast light into a detector, the optical analyzer characterized in that a light-emitting semiconductor device is used as the light source and an optical filter is provided in an optical path from the light source to the detector, the optical filter having such a characteristic as to allow passage of light having a wavelength within a range centering on the wavelength of a peak having a highest intensity in an emission spectrum of the light source and having an intensity equal to or higher than 70% of the highest intensity and to block passage of light having a wavelength outside the aforementioned range.

By determining the passband width of the optical filter in this manner, a concentration linearity that is comparable or close to a high-accuracy absorbance detector can be achieved.

Advantageous Effects of the Invention

In the optical analyzer according to the first aspect of the present invention, the optical filter removes light within a wavelength region where the amount of light considerably changes with time, so that the detection signal obtained with the detector contains a lower level of noise and drift originating from the light source than in the conventional case. As a result, a high level of analytical accuracy is achieved despite the use of an LED or similar light-emitting semiconductor device as the light source.

In the optical analyzer according to the second aspect of the present invention, the optical filter removes the light within the wavelength regions corresponding to the base portions of a peak in the emission spectrum while allowing the light within a narrow wavelength width around the peak wavelength to reach the detector, whereby the amount of stray light is reduced. Therefore, while using an LED or similar light-emitting semiconductor device as the light source, the linearity of absorption can be improved without using any light-dispersing device or monochromator.

DESCRIPTION OF EMBODIMENTS

Embodiments of the optical analyzer according to the present invention are hereinafter described with reference to the attached drawings.

Figure 1:
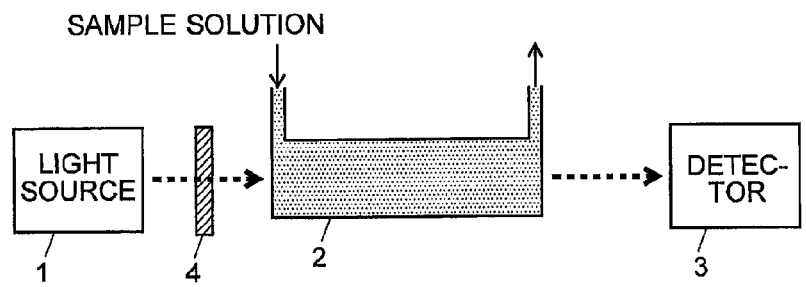
FIG. 1 is a schematic configuration diagram of an absorptiometer as one embodiment of the optical analyzer according to the present invention.

FIG. 1 is a schematic configuration diagram of an absorptiometer as one embodiment of the present invention.

Light emitted from a light source unit 1 is passed through an optical filter 4. The transmitted light is cast as measurement light into a sample cell 2 through which a sample solution to be analyzed is flowing. The portion of light which has passed through the sample cell 2 reaches a detector 3. While passing through the sample cell 2, the measurement light undergoes absorption depending on the kinds, concentrations and other properties of the sample components in the sample cell 2. The light which has undergone the absorption enters the detector 3, which generates a detection signal corresponding to the amount of incident light.

The light source unit 1 includes a deep ultraviolet LED as the light source. One example of the emission spectrum of the deep ultraviolet LED is shown by the broken line in FIG. 2. The central wavelength of the peak showing the highest intensity which is used as the measurement light is approximately 280 nm and hence within the deep ultraviolet region. Additionally, a peak of unwanted light whose intensity is less than one hundredth of the main peak exists around a wavelength range of 440 to 450 nm, which is within the visible region.

The optical filter 4 is used to remove this unwanted light. It is an ultraviolet-transmitting visible-absorbing filter, a kind of shortpass filter. Placing this optical filter 4 in the optical path causes the spectrum of the measurement light cast into the sample cell 2 to change as shown by the solid line in FIG. 2. That is to say, the components of light with wavelengths equal to or longer than approximately 380 nm are dramatically weakened (in the present example, to one tenth or less of the intensity observed without the optical filter 4). As a result, measurement light which forms an isolated peak having the highest intensity near 280 nm and hence can be regarded as almost monochromatic is cast into the sample cell 2.

In general, the temporal change in the intensity of the main peak near 280 nm is small, while the temporal change in the intensity of a peak of unwanted light which is different from the main peak is comparatively large. In the absorptiometer of the present embodiment, the amount of light across the entire wavelength range of the measurement light cast into the sample cell 2 (to be exact, the entire wavelength range within which the detector 3 has detection sensitivity) is reflected in the detection signal. Therefore, if a component of light whose amount considerably changes is present within the wavelength range of the measurement light, the detection signal is likely to be affected by the change. By contrast, in the present absorptiometer, the measurement light is free of light whose amount considerably changes with time, since the optical filter 4 blocks light within a wavelength region where the amount of light considerably changes with time. Therefore, the temporal change in the detection signal is suppressed regardless of the degree of absorption of light in the sample cell 2.

Figure 3:
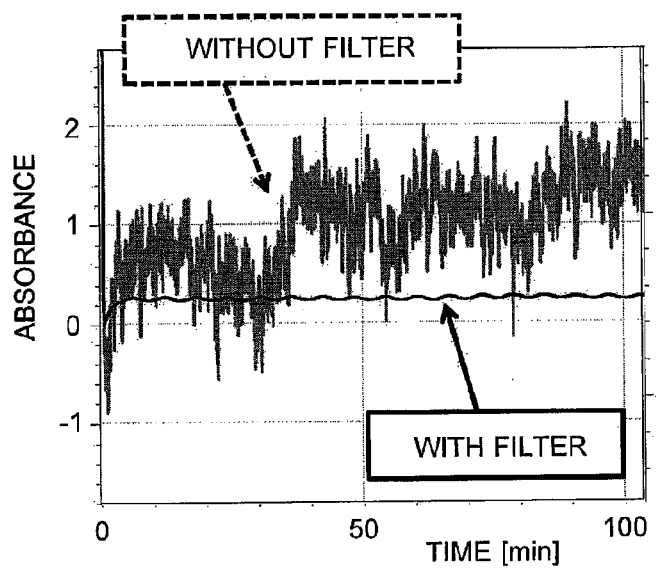
FIG. 3 is a graph showing an actually measured example of the temporal change in the absorbance calculated from detection signals in the absorptiometer of the present embodiment.

FIG. 3 shows an actually measured example of the temporal change in the absorbance calculated from detection signals in the case where the optical filter 4 was provided and the case where the filter was not provided. The result demonstrates that the use of the optical filter 4 reduces the noise and dramatically suppresses the drift. Thus, in the absorptiometer of the present embodiment, the effects of the noise and drift originating from the LED used in the light source unit 1 are reduced, so that the analytical accuracy is improved.

As explained previously, the amount of light of an LED is normally temperature dependent. To reduce the influence of temperature, it is preferable to perform a temperature control for roughly maintaining a fixed temperature of the LED in the light source unit 1, or a feedback control in which a portion of the light emitted from the LED is monitored and the drive current to the LED is regulated so as to roughly maintain the monitored light at a fixed amount (although such a control system is not shown in FIG. 1). Naturally, the temperature control of the LED and the feedback control of the drive current may be simultaneously performed. In the case where the absorptiometer of the present embodiment is used as a detector for a liquid chromatograph, it is possible to place the present absorptiometer inside the column oven used for maintaining a column at an approximately fixed temperature, in which case the temperature of the light source unit 1 can be controlled by the column oven.

Figure 4:
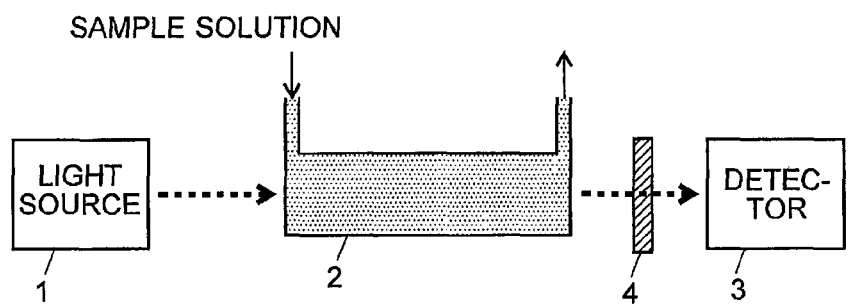
FIG. 4 is a schematic configuration diagram of an absorptiometer as another embodiment of the optical analyzer according to the present invention.

In the previous embodiment, the optical filter 4 is placed in the optical path between the light source unit 1 and the sample cell 2. What is required is to prevent entry into the detector 3 of the light within the wavelength region including a peak at which the amount of light considerably changes with time. Therefore, the optical filter 4 may also be placed in the optical path between the sample cell 2 and the detector 3, as in the absorptiometer of another embodiment shown in FIG. 4.

Figure 5:
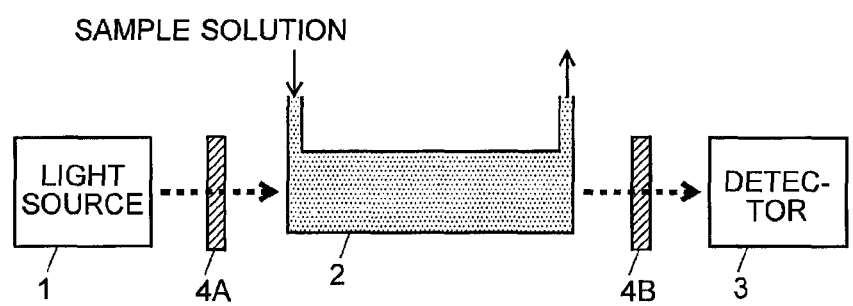
FIG. 5 is a schematic configuration diagram of an absorptiometer as still another embodiment of the optical analyzer according to the present invention.

Furthermore, as in the absorptiometer of still another embodiment shown in FIG. 5, two optical filters 4A and 4B may be respectively placed in both the optical path between the light source unit 1 and the sample cell 2 and the optical path between the sample cell 2 and the detector 3. This configuration can effectively prevent a wavelength of light whose amount considerably changes with time from entering the detector 3 in the form of stray light.

Figure 6:
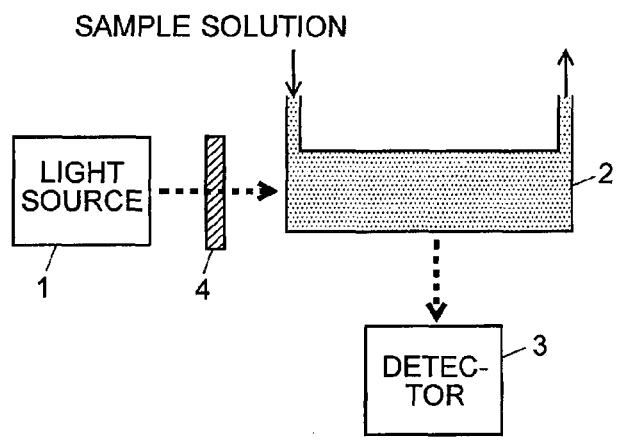
FIG. 6 is a schematic configuration diagram of a fluorometer as still another embodiment of the optical analyzer according to the present invention.

FIG. 6 is a schematic configuration diagram of a fluorometer as still another embodiment of the present invention.

In this fluorometer, the light emitted from the light source unit 1 is passed through the optical filter 4 and cast as excitation light into the sample cell 2 through which a sample solution is to be analyzed is flowing. The sample components in the sample cell 2 are excited by the excitation light and emit fluorescent light. This light enters the detector 3, which generates a detection signal corresponding to the amount of incident light. Similarly to the case of the absorptiometer shown in FIG. 1, the excitation light cast into the sample cell 2 does not contain unwanted light within a wavelength region where the amount of light considerably changes with time. Therefore, there is no scattered light or the like originating from the unwanted light and reaching the detector 3. As a result, the noise and drift in the detection signal are reduced.

The present invention is generally applicable in any optical analyzers which detect various kinds of light obtained from a sample in response to measurement light cast into or onto the sample, including not only the transmitted light that has undergone absorption by sample components and the fluorescent light but also the scattered light, diffracted light and others.

In any of the previous embodiments, the light blocked by the optical filter 4, 4A and/or 4B belongs to a wavelength region corresponding to the peak of unwanted light whose wavelength is to some extent separated from the main peak. Therefore, for example, in the spectrum shown in FIG. 2, the light within the wavelength range of the main peak having the peak top at approximately 280 nm is almost entirely used as measurement light. However, it is also possible to use, as the optical filter 4, 4A and/or 4B, a bandpass filter having a narrower passband width than the peak width of the main peak centering on the peak-top wavelength, in order to further decrease the noise and drift in the detection signal.

Figure 7A:
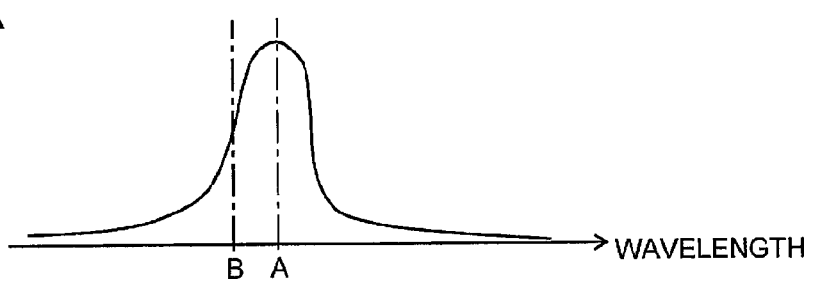
FIGS. 7A and 7B are graphs showing an actually measured example of the temporal change in the absorbance calculated from the detection signals at wavelength A of the peak top and at wavelength B at which the signal intensity is equal to one half of the peak-top intensity.
Figure 7B:
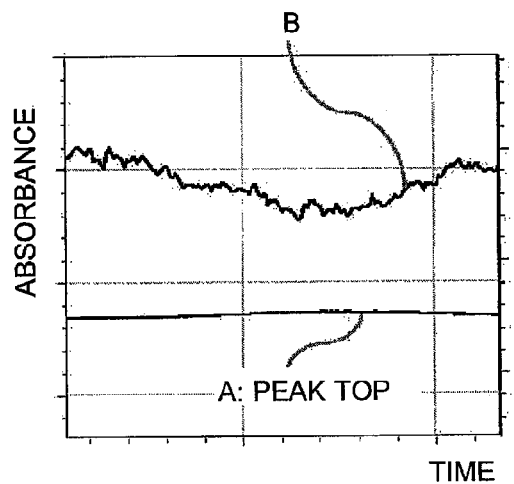

FIG. 7B shows an actually measured example of the temporal change in the absorbance calculated from the detection signals at the peak-top wavelength A of the main peak and at wavelength B at which the signal intensity is equal to one half of the peak-top intensity (see FIG. 7A).

FIG. 7B shows that the temporal fluctuation in the amount of light at a wavelength in the base portion of the peak is considerably greater than at the peak-top wavelength. In LEDs, such a fluctuation in the amount of light generally tends to be greater with an increase in the distance from the wavelength of the peak top showing the highest intensity. This fluctuation in the amount of light also contributes the noise and drift. Therefore, by using a bandpass filter having the previously described wavelength characteristic which leaves the light included in a predetermined passband width narrower than the peak width centering on the peak-top wavelength and weakens (or removes) the light within the outer wavelength regions, the influence of the fluctuation in the amount of light on the detection signal can be reduced, whereby the noise and drift can be further lowered.

A bandpass filter having a passband width of approximately ±5 nm around a central wavelength is commercially available. By using such a bandpass filter, the previously described influence of the fluctuation in the amount of light can be considerably reduced.

If the absorption wavelength of the sample roughly coincides with the peak-top wavelength of the main peak in the emission spectrum of the light source unit 1, it is possible to improve the linearity of absorption by using a bandpass filter having the previously described bandpass width as the optical filter 4, 4A and/or 4B to remove the wavelengths in the base portions of the main peak on both longer and shorter wavelength sides of the peak top in the emission spectrum.

The reason is as follows: In the present case, other wavelengths of light near the absorption peak also undergo absorption by the sample. However, the absorbance index at those wavelengths is lower than at the absorption peak. Therefore, if the degree of absorption by the sample is high and the intensity of the light having the absorption wavelength is accordingly low, the light having wavelengths near the absorption peak will be considerably influential as stray light, and consequently, the linearity of absorption will deteriorate. Such an influence of the stray light can be reduced, and the linearity can be accordingly improved, by using a bandpass filter in the previously described manner to remove light having wavelengths which are separated from the absorption peak by an amount equal to or greater than predetermined.

Figure 2:
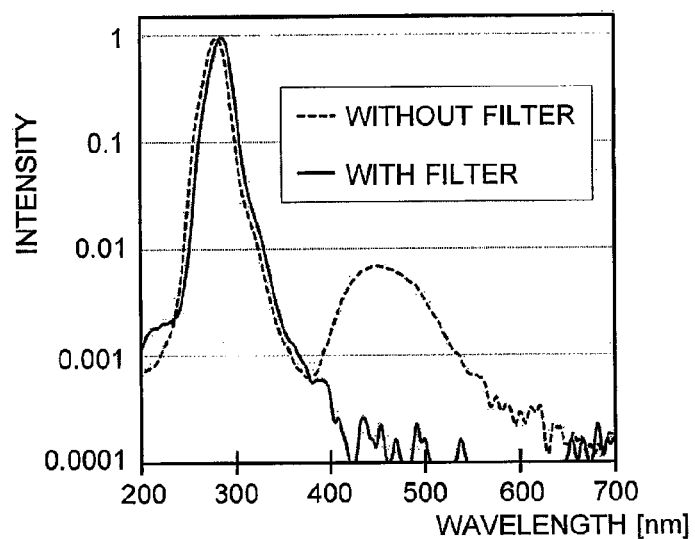
FIG. 2 is a graph showing an actually measured example of the spectrum of measurement light in the absorptiometer of the present embodiment.
Figure 8:
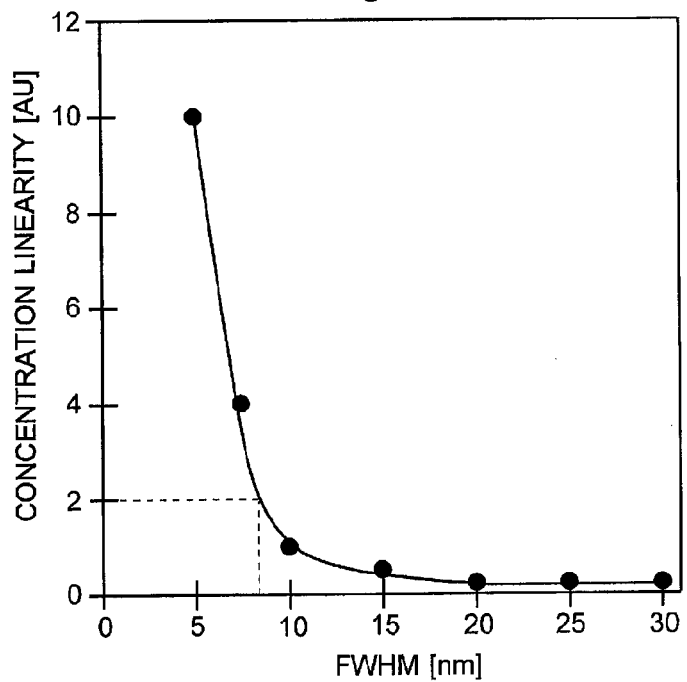
FIG. 8 is a graph showing the relationship between the full width at half maximum of illumination light and the concentration linearity.

FIG. 8 is a graph showing a relationship between the full width at half maximum (FWHM) at the wavelength of the light cast into the sample and the concentration linearity of the measured value. In the present example, the FWHM of the absorbance spectrum of the sample is 30 nm. FIG. 8 demonstrates that the concentration linearity rapidly decreases as the FWHM of the cast light increases from 5 nm to 15 nm. A high-accuracy photodiode array (PDA) detector has a concentration linearity of approximately 2 [AU]. According to FIG. 8, this level of performance can be achieved with a FWHM of approximately 8 nm. In FIG. 2, the spectrum of the measurement light obtained using the optical filter has a FWHM of 8 nm at an intensity of approximately 0.7 to 0.8. Accordingly, to achieve a concentration linearity comparable or close to a high-accuracy PDA detector, the passband width of the optical filter 4 can be determined so as to allow passage of a range of wavelengths of light centering on the wavelength of the highest-intensity peak in the emission spectrum and having an intensity equal to or higher than approximately 70% of the highest intensity.

Naturally, it is possible to construct an optical filter having the previously described wavelength characteristic using a combination of a longpass filter and a shortpass filter instead of a bandpass filter. For example, in the absorptiometer shown in FIG. 5, a longpass filter may be used as the optical filter 4A and a shortpass filter, as the optical filter 4B.

Although an LED is used as the light source in any of the previous embodiments, an optical analyzer using a light-emitting semiconductor device other than the LED, such as a super luminescence diode (SLD) or laser diode (LD), as the light source can also be constructed in a similar fashion to reduce the influence of the noise and drift originating from those devices.

It should be noted that any of the previous embodiments and their variations are mere examples of the present invention and will naturally fall within the scope of claims of the present application even if a change, modification or addition is appropriately made within the spirit of the present invention.

REFERENCE SIGNS LIST

1 . . . Light Source Unit
2 . . . Sample Cell
3 . . . Detector
4, 4A, 4B . . . Optical Filter

The invention claimed is:

1. An optical analyzer for analyzing a target sample by casting light from a light source into or onto the sample and introducing light obtained from the sample in response to the cast light into a detector, wherein:

a light-emitting semiconductor device is used as the light source and an optical filter is provided in an optical path from the light source to the detector, the optical filter blocking light within a range of wavelengths longer than a wavelength of a peak having a highest intensity in an emission spectrum of the light source, within a range of wavelengths shorter than the wavelength of the highest-intensity peak or within a range of wavelengths longer and shorter than the wavelength of the highest-intensity peak, and each of the ranges of wavelengths including a peak at which a temporal change in an amount of light is larger than that at the highest-intensity peak, and the optical filter has such a characteristic of allowing passage of light within a predetermined wavelength width centering on the wavelength of the highest-intensity peak and being narrower than a full width at half maximum of the highest-intensity peak and of blocking light within wavelength regions outside the aforementioned wavelength width.

2. The optical analyzer according to claim 1, wherein:
the optical filter has such a characteristic as to block light at a peak appearing within a range of wavelengths longer than the wavelength of the highest-intensity peak in the emission spectrum of the light source.

3. An optical analyzer for analyzing a target sample by casting light from a light source into or onto the sample and introducing light obtained from the sample in response to the cast light into a detector, wherein:
a light-emitting semiconductor device is used as the light source and an optical filter is provided in an optical path from the light source to the detector, the optical filter having such a characteristic as to allow passage of light having a wavelength within a range centering on a wavelength of a peak having a highest intensity in an emission spectrum of the light source and having an intensity equal to or higher than 70% of the highest intensity and to block passage of light having a wavelength outside the aforementioned range.

* * * * *